(12) United States Patent
Grostefon et al.

(10) Patent No.: US 9,937,048 B2
(45) Date of Patent: Apr. 10, 2018

(54) FEMORAL STEM INCLUDING AN ANCHOR TO FACILITATE ASSEMBLY AND IMPLANTATION

(71) Applicants: Justin D. Grostefon, Columbia City, IN (US); Rodney E. Satterthwaite, Huntington, IN (US); Jeffrey A. McAnelly, Columbia City, IN (US); Jeffrey R. Roose, Milford, IN (US); Edward Kavanagh, Warsaw, IN (US); Theodore L. Badgley, Fort Wayne, IN (US)

(72) Inventors: Justin D. Grostefon, Columbia City, IN (US); Rodney E. Satterthwaite, Huntington, IN (US); Jeffrey A. McAnelly, Columbia City, IN (US); Jeffrey R. Roose, Milford, IN (US); Edward Kavanagh, Warsaw, IN (US); Theodore L. Badgley, Fort Wayne, IN (US)

(73) Assignee: DEPUY IRELAND UNLIMITED COMPANY (IE)

( * ) Notice: Subject to any disclaimer, the term of this patent is extended or adjusted under 35 U.S.C. 154(b) by 0 days.

(21) Appl. No.: 14/995,518

(22) Filed: Jan. 14, 2016

(65) Prior Publication Data
US 2016/0206433 A1    Jul. 21, 2016

Related U.S. Application Data

(60) Provisional application No. 62/103,826, filed on Jan. 15, 2015.

(51) Int. Cl.
*A61F 2/36* (2006.01)
*A61F 2/46* (2006.01)
*A61F 2/30* (2006.01)

(52) U.S. Cl.
CPC ............ *A61F 2/367* (2013.01); *A61F 2/3607* (2013.01); *A61F 2/3609* (2013.01);
(Continued)

(58) Field of Classification Search
CPC .................. A61F 2/4607; A61F 2/4612; A61F 2002/368; A61F 2002/3627;
(Continued)

(56) References Cited

U.S. PATENT DOCUMENTS 1,435,278 A    11/1922    Campbell
1,595,658 A    8/1926    Heinrich
(Continued)

FOREIGN PATENT DOCUMENTS

DE    29824993 U1    1/2004
DE    202012102017 U1    10/2013
(Continued)

OTHER PUBLICATIONS

PCT Search Report for International Application No. PCT/US2016/013381, dated Apr. 15, 2016, 6 pages.
(Continued)

*Primary Examiner* — Thomas J Sweet
*Assistant Examiner* — Megan Wolf
(74) *Attorney, Agent, or Firm* — Barnes & Thornburg LLP

(57) ABSTRACT

An orthopedic prosthesis for use in a hip replacement surgery. The orthopedic prosthesis includes an elongated stem component that has a proximal body, a neck extending superiorly and medially from the proximal body and a tapered stem extending inferiorly from the proximal body. An anchor is positioned on the neck and is configured to be engaged by a surgical instrument. A system for use in assembling the orthopedic prosthesis and a method of assembly are also disclosed.

6 Claims, 10 Drawing Sheets

(52) U.S. Cl.
CPC .. *A61F 2/4637* (2013.01); *A61F 2002/30332* (2013.01); *A61F 2002/30879* (2013.01); *A61F 2002/365* (2013.01); *A61F 2002/368* (2013.01); *A61F 2002/3625* (2013.01); *A61F 2002/3627* (2013.01); *A61F 2002/3631* (2013.01); *A61F 2002/3641* (2013.01); *A61F 2002/3654* (2013.01); *A61F 2002/4627* (2013.01); *A61F 2002/4666* (2013.01)

(58) Field of Classification Search
CPC ...... A61F 2002/3639; A61F 2002/3641; A61F 2002/3643
See application file for complete search history.

(56) References Cited

U.S. PATENT DOCUMENTS

| | | | |
|---|---|---|---|
| 1,794,494 | A | 3/1931 | Noble |
| 2,190,585 | A | 2/1940 | Rhinevault |
| 2,408,801 | A | 10/1946 | Miller |
| 2,863,477 | A | 12/1958 | Sagerty |
| 3,102,536 | A | 9/1963 | Rose et al. |
| 3,801,989 | A | 4/1974 | McGee |
| 4,705,520 | A | 11/1987 | Ahrens |
| 4,795,472 | A | 1/1989 | Crowninshield et al. |
| 4,865,609 | A | 9/1989 | Roche |
| 5,133,765 | A | 7/1992 | Cuilleron |
| 5,171,324 | A | 12/1992 | Campana et al. |
| 5,849,015 | A * | 12/1998 | Haywood ............ A61F 2/4607 606/99 |
| 5,966,792 | A | 10/1999 | James |
| 6,113,605 | A * | 9/2000 | Storer ................ A61F 2/4607 606/86 R |
| 6,629,982 | B2 | 10/2003 | Day et al. |
| 7,497,875 | B1 | 3/2009 | Zweymuller |
| 7,661,162 | B2 | 2/2010 | Soerensen et al. |
| 7,699,847 | B2 | 4/2010 | Sheldon et al. |
| 8,152,855 | B2 | 4/2012 | Tulkis et al. |
| 8,518,050 | B2 | 8/2013 | McCleary et al. |
| 8,533,921 | B2 | 9/2013 | Leisinger et al. |
| 2004/0267373 | A1 | 12/2004 | Dwyer et al. |
| 2007/0162038 | A1* | 7/2007 | Tuke ................... A61F 2/4607 606/88 |
| 2009/0281632 | A1 | 11/2009 | Naidu |
| 2011/0009976 | A1 | 1/2011 | Cruchet |
| 2012/0253469 | A1 | 10/2012 | Collins |
| 2012/0259338 | A1 | 10/2012 | Carr et al. |
| 2016/0206430 | A1 | 7/2016 | Grostefon et al. |
| 2016/0206443 | A1 | 7/2016 | Brooks et al. |
| 2016/0206444 | A1 | 7/2016 | Schmalzried |
| 2016/0206445 | A1* | 7/2016 | Gheevarughese .... A61F 2/3094 |

FOREIGN PATENT DOCUMENTS

| | | |
|---|---|---|
| EP | 0200672 A1 | 11/1986 |
| EP | 1080701 A2 | 3/2001 |
| EP | 1437107 A1 | 7/2004 |
| EP | 1776937 A1 | 4/2007 |
| WO | 0059410 A2 | 12/2000 |
| WO | 2016115359 A1 | 7/2016 |
| WO | 2016115364 A1 | 7/2016 |
| WO | 2016115365 A1 | 7/2016 |

OTHER PUBLICATIONS

PCT Search Report for International Application No. PCT/US2016/013427, dated May 17, 2016, 5 pages.
PCT Search Report for International Application No. PCT/US2016/013433, dated May 17, 2016, 6 pages.
PCT Search Report for International Application No. PCT/US2016/013434, dated May 23, 2016, 6 pages.

* cited by examiner

US 9,937,048 B2

FEMORAL STEM INCLUDING AN ANCHOR TO FACILITATE ASSEMBLY AND IMPLANTATION

This application claims priority under 35 U.S.C. § 119 to U.S. Patent App. Ser. No. 62/103,826 entitled "FEMORAL STEM INCLUDING AN ANCHOR TO FACILITATE ASSEMBLY AND IMPLANTATION," which was filed Jan. 15, 2015 and is expressly incorporated herein by reference.

CROSS-REFERENCE

Cross-reference is made to U.S. Patent App. Ser. No. 62/103,611 entitled "ASSEMBLY TOOL," which was filed Jan. 15, 2015 and is expressly incorporated herein by reference.

TECHNICAL FIELD

The present disclosure relates generally to orthopaedic prostheses, and particularly to orthopaedic prostheses for use in hip replacement surgery.

BACKGROUND

Joint arthroplasty is a well-known surgical procedure by which a diseased and/or damaged natural joint is replaced by a prosthetic joint. The prosthetic joint may include a prosthesis that is implanted into one or more of the patient's bones. Many hip prostheses include a femoral prosthesis that is implanted into a patient's femur. A femoral prosthesis typically includes an elongated stem component that is received in the medullary canal of the patient's femur and a spherically-shaped head component that bears against the patient's acetabulum or a prosthetic replacement acetabular cup.

The elongated stem implant may be cemented into the medullary canal or may have a porous coated surface for allowing the bone to heal directly to the implant. In some prostheses, the head is attached to a neck of the elongated stem via a taper connection. It is important to assemble the head to the neck with enough force so as to limit micromotion between the head and neck. The acetabulum of the patient may also be reamed to receive a shell and liner. A polyethylene, metal or ceramic liner with a metal shell is inserted into the acetabulum and acts as socket for receiving the head on the stemmed implant.

SUMMARY

According to one aspect of the disclosure, an orthopaedic prosthesis is disclosed. The orthopaedic prosthesis comprises an elongated stem component. The elongated stem component includes a proximal body and a neck extending superiorly and medially from the proximal body. The neck has a longitudinal axis and is configured to receive a femoral head component. The stem component also includes a tapered stem extending inferiorly from the proximal body, and an anchor positioned on the neck. The anchor extends orthogonal to the longitudinal axis of the neck.

In some embodiments, the anchor may include a first flange positioned on an anterior side of the neck and a second flange positioned on a posterior side of the neck. In some embodiments, the first flange may extend outwardly from the anterior side of the neck, and the second flange may extend outwardly from the posterior side of the neck. Additionally, in some embodiments, a first opening may be defined in the anterior side of the neck, and the first flange may include a first inner wall extending inwardly from the first opening.

In some embodiments, a second opening may be defined in the posterior side of the neck, and the second flange may include a second inner wall extending inwardly from the second opening.

In some embodiments, the first flange and the second flange may include engagement surfaces that are positioned in an imaginary plane extending orthogonal to the longitudinal axis of the neck.

In some embodiments, the neck may include a first opening defined in an anterior surface, a second opening defined in a posterior surface, and the anchor may include an inner wall that extends between the first opening and the second opening.

In some embodiments, the inner wall may include a substantially planar medial surface and a curved surface connected to the substantially planar medial surface. Additionally, in some embodiments, the neck may extend from a superior tip to an inferior end attached to the proximal body, and the anchor may be positioned on the medial side of the inferior end of the neck.

In some embodiments, the anchor may include a medial collar extending outwardly from the inferior end of the neck. In some embodiments, an opening may be defined in the inferior end of the neck, and the anchor may include an inner wall that extends inwardly from the opening.

In some embodiments, the proximal body may have a first opening defined in an anterior side and a second opening defined in a posterior side adjacent to the neck. The neck may include a first inner wall that extends inwardly from the first opening and a second inner wall that extends inwardly from the second opening. The anchor may include the first inner wall and the second inner wall.

In some embodiments, the orthopaedic prosthesis may include the femoral head component including a tapered bore. The neck may include a tapered trunnion sized to receive the tapered bore.

According to another aspect, a system for hip orthopaedic surgery is disclosed. The system includes a femoral head component, an elongated stem component, and a surgical instrument. The elongated stem component includes a proximal body, a neck extending superiorly and medially from the proximal body, a tapered stem extending inferiorly from the proximal body, and an anchor positioned on the neck and extending orthogonal to the longitudinal axis of the neck. The neck is configured to receive the femoral head component.

The surgical instrument includes a plate configured to engage the femoral head component, an arm configured to engage the anchor to secure the surgical instrument to the elongated stem component, and an actuator configured to move the plate along an axis to apply a force to the femoral head component.

In some embodiments, the anchor may include a first flange positioned on an anterior side of the neck and a second flange positioned on a posterior side of the neck. The arm of the surgical instrument may be a first arm configured to engage the first flange, and the surgical instrument may include a second arm configured to engage the second flange.

In some embodiments, the proximal body may have a first opening defined in an anterior side and a second opening defined in a posterior side adjacent to the neck. The neck may include a first inner wall that extends inwardly from the first opening and a second inner wall that extends inwardly from the second opening. The anchor may include the first inner wall and the second inner wall.

According to another aspect, an orthopaedic prosthesis comprises a femoral head component and an elongated stem component. The elongated stem component comprises a proximal body, a neck that is configured to receive the femoral head component and extending superiorly and medially from the proximal body, and a tapered stem extending inferiorly from the proximal body. A first opening is defined an anterior surface of the neck, a second opening is defined in a posterior surface of the neck, and a pair of inner walls extend inwardly from the first opening and the second opening. Each inner wall includes a medial surface positioned in an imaginary plane extending orthogonal to the longitudinal axis of the neck.

In some embodiments, the pair of inner walls may define a single inner wall extending from the first opening between the second opening.

BRIEF DESCRIPTION OF THE DRAWINGS

The detailed description particularly refers to the following figures, in which.

DETAILED DESCRIPTION OF THE DRAWINGS

Figure 1:
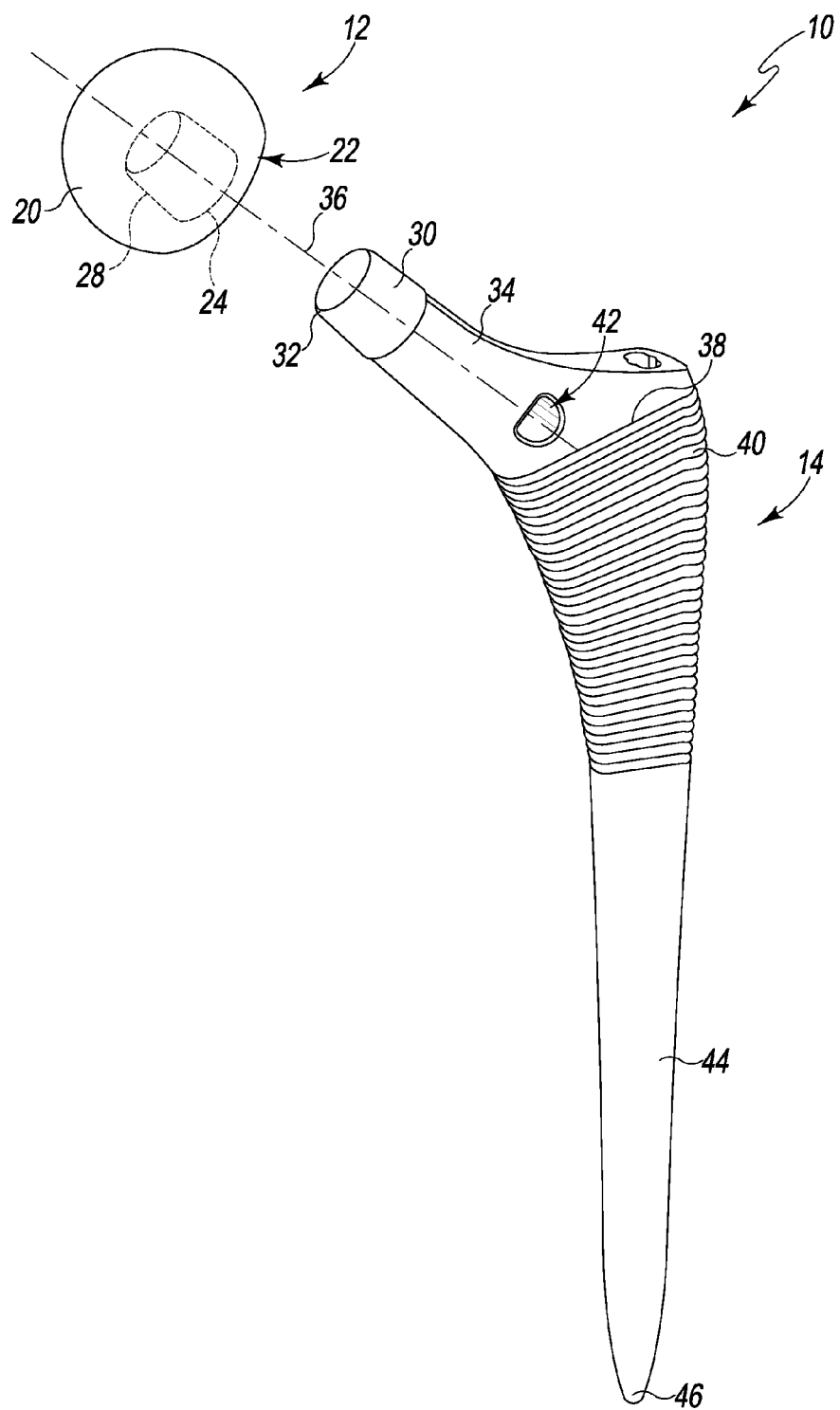
FIG. 1 is a perspective view of an orthopaedic implant.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants or prostheses and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Referring to FIG. 1, an orthopaedic prosthesis is illustratively embodied as a femoral orthopaedic implant 10 of a hip prosthesis. The femoral orthopaedic implant 10 (hereinafter implant 10) includes a head component 12 and an elongated stem component 14 that is configured to be inserted into an intramedullary canal 16 of a patient's surgically-prepared femur 18. In particular, the femoral stem component 14 is implanted into a surgically prepared (e.g., broached) intramedullary canal 16 of the patient's femur 18.

The head component 12 includes a spherical outer surface 20 configured to engage a patient's natural acetabulum (not shown) or a prosthetic acetabular cup implanted into the patient's pelvic bone. The head component 12 may be constructed with an implant-grade biocompatible metal, although other materials may also be used. Examples of such metals include cobalt, including cobalt alloys such as a cobalt chrome alloy, titanium, including titanium alloys such as a Ti6Al4V alloy, and stainless steel. The head component 12 also includes a distal surface 22 having an opening 24 defined therein, and an inner wall extends inwardly from the opening 24 to define a tapered bore 28 in the head component 12.

The head component 12 is secured to a trunnion 30 formed in the end 32 of the elongated neck 34 of the stem component 14. As shown in FIG. 1, the elongated neck 34 has a longitudinal axis 36 that extends through the trunnion 30. In the illustrative embodiment, the head component 12 is advanced along the longitudinal axis 36 to advance the tapered trunnion 30 of the stem component 14 may be advanced into the tapered bore 28 of the head component 12 to taper lock the trunnion 30 (and hence the stem component 14) and the femoral head component 12 to one another. When installed on the stem component 14, the femoral head component 12 is positioned to bear on either the patient's natural acetabulum or a prosthetic socket which has been implanted into the patient's pelvis to replace his or her acetabulum. In such a manner, the orthopaedic hip prosthesis 10 and the natural or artificial acetabulum collectively function as a system which replaces the natural joint of the patient's hip As shown in FIG. 1, the elongated neck 34 extends medially and superiorly from an inferior end 38 attached to a proximal body 40 of the elongated stem component 14. As described in greater detail below, the elongated stem component 14 also includes a tool engagement feature or anchor 42 that is positioned on the neck 34. A tapered stem 44 extends inferiorly away from the opposite end of the proximal body. The tapered stem 44 has a rounded distal end 46 that defines the inferior-most surface of the femoral stem component 14.

In the illustrative embodiment described herein, the stem component 14 is embodied as a "fit and fill" type of femoral stem. As such, the stem component 14 is embodied as a monolithic metal structure. The stem component 14 may be constructed with an implant-grade biocompatible metal, although other materials may also be used. Examples of such metals include cobalt, including cobalt alloys such as a cobalt chrome alloy, titanium, including titanium alloys such as a Ti6Al4V alloy, and stainless steel. Such a metallic femoral stem component 14 may also be coated with a surface treatment, such as hydroxyapatite, to enhance biocompatibility. Moreover, the surfaces of the femoral stem component 14 that engage the natural bone, such as the outer surface of the proximal body 40, may be textured to facilitate securing the component to the bone. Such surfaces may also be porous coated to promote bone ingrowth for permanent fixation.

Figure 2A:
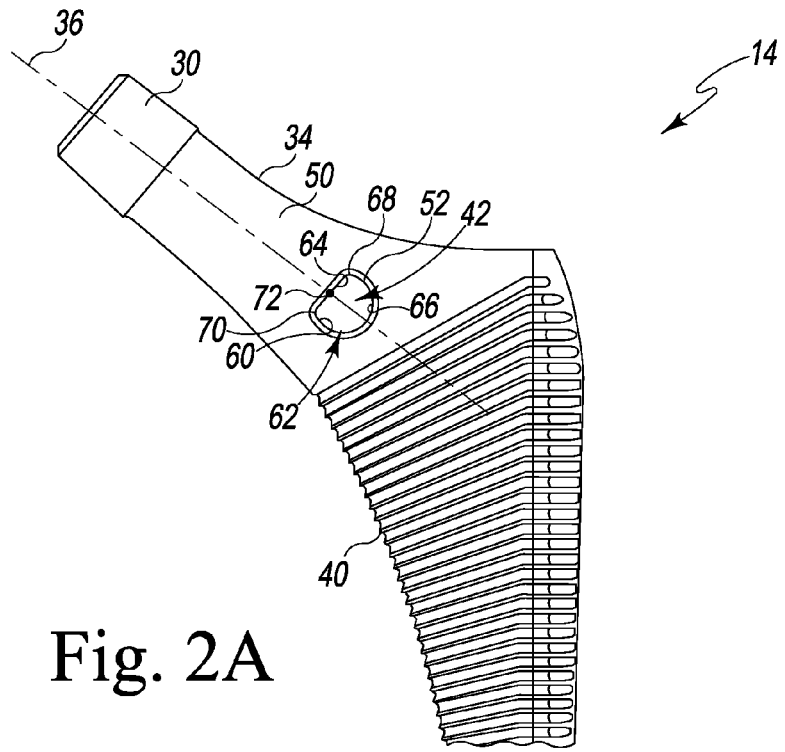
FIG. 2A is an anterior side elevation view of the orthopaedic implant of FIG. 1.
Figure 2B:
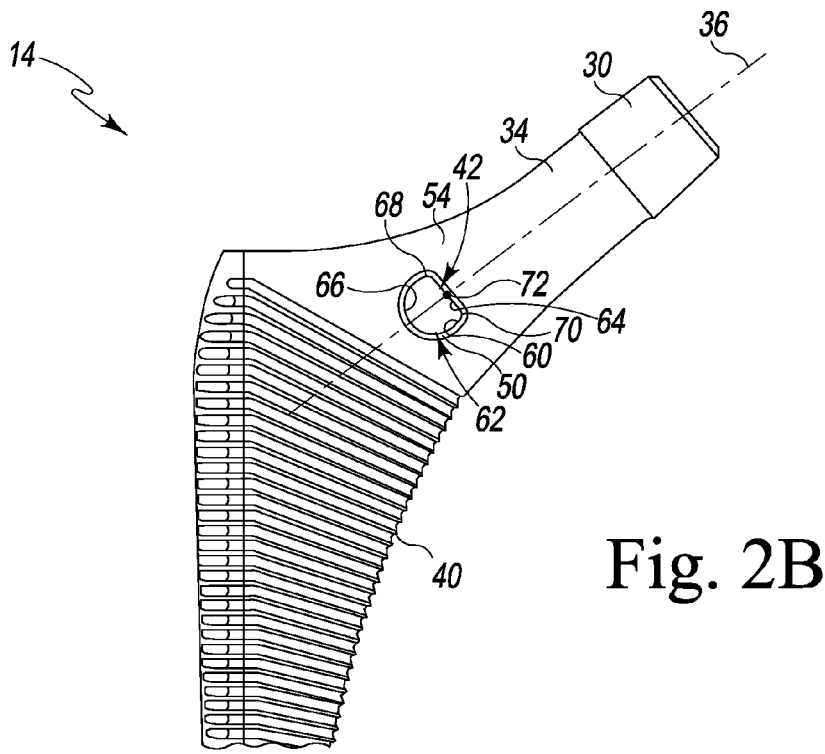
FIG. 2B is a posterior side elevation view of the orthopaedic implant of FIG. 1.

As shown in FIGS. 2A and 2B, the anchor 42 of the elongated stem component 14 is defined in an anterior surface 50 and a posterior surface 54. The anterior surface 50 of the stem component 14 extends from the inferior end 38 of the neck 34 to the base of the trunnion 30, and an opening 52 is defined in the anterior surface 50 adjacent to the inferior end 38 of the neck 34. The posterior surface 54 extends from the inferior end 38 of the neck 34 to the base of the trunnion 30. Another opening 56 is defined in the posterior surface 54 adjacent to the inferior end 38 of the neck 34. In the illustrative embodiment, the anchor 42 includes an inner wall 60 that extends inwardly from the openings 52, 56. As shown in FIGS. 2A and 2B, the inner wall 60 defines a passageway 62 through the elongated neck 34.

The inner wall 60 includes a medial surface 64 and a curved lateral surface 66 that extend between the openings 52, 56. In the illustrative embodiment, the medial surface 64 is substantially planar and extends orthogonal to the longitudinal axis 36 of the elongated neck 34. In other embodiments, the medial surface 64 (and hence the anchor 42) may merely extend transverse to the axis 36. Additionally, as shown in FIGS. 2A and 2B, the medial surface 64 extends between a superior edge 68 and an inferior edge 70 that are connected to the lateral surface 66. In the illustrative embodiment, the longitudinal axis 36 intersects the medial surface 64 at a midpoint 72 on the surface 64 between the edges 68, 70. It should be appreciated that in other embodiments the axis 36 may be offset from the midpoint 72

Figure 3:
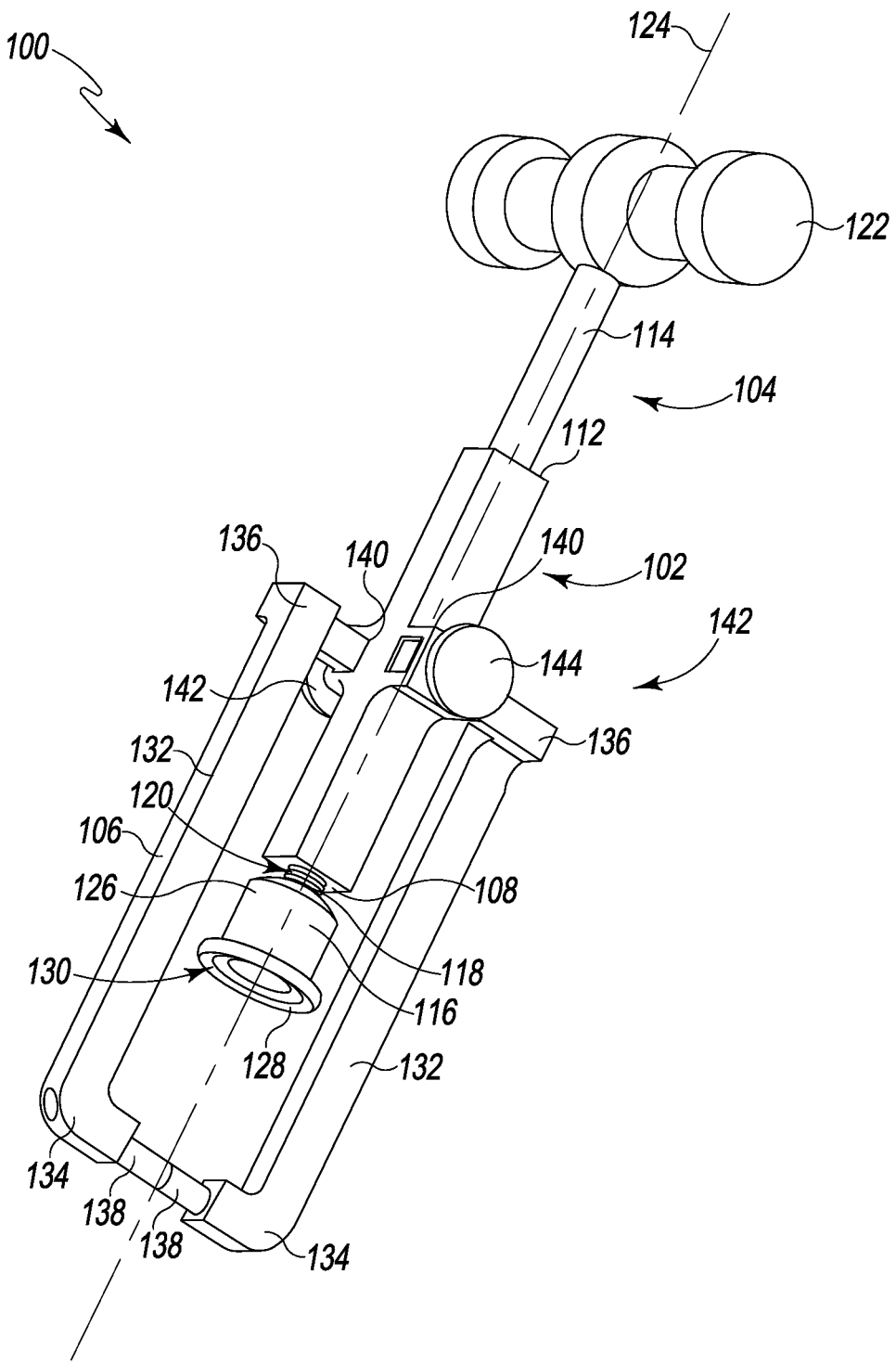
FIG. 3 is a perspective view of a surgical instrument for use with the orthopaedic implant of FIG. 1.

Referring now to FIG. 3, a surgical instrument 100 for use in securing the femoral head component 12 to the elongated stem component 14 is shown. The surgical instrument 100 includes a body 102, an actuator 104 configured to engage the femoral head component 12, and a pair of elongated arms 106 configured to engage the anchor 42 of the elongated stem component 14. The body 102 of the instrument 100 includes an elongated bore 108 that extends from a distal end 110 to a proximal end 112. In the illustrative embodiment, the elongated bore 108 is internally-threaded at the distal end 110.

The actuator 104 of the instrument 100 has a shaft 114 that extends through the elongated bore 108 and an engagement plate 116 that is attached to the distal end 118 of the shaft 114. The distal end 118 of the shaft 114 includes a plurality of external threads 120 that are configured to engage the internally-threaded bore 108 of the body 102. A handle 122 is secured to the shaft 114 at the end opposite the distal end 118. As described in greater detail below, the handle 122 is operable to rotate the shaft 114 and move the engagement plate 116 along an axis 124 defined by the shaft 114.

As shown in FIG. 3, the engagement plate 116 includes a base 126 that is secured to the distal end 118 of the shaft 114. The plate 116 also includes a distal surface 128 that is configured to engage the femoral head component 12. In the illustrative embodiment, the distal surface 128 is concave to define a recess 130 that receive the spherical outer surface 20 of the femoral head component 12. The engagement plate 116 is illustratively formed from a polymeric material such as a hard plastic. It should be appreciated that in other embodiments the plate 116 may be partially or fully formed from a metallic material. In other embodiments, the plate 116 may also include a gasket formed from an elastomeric material, which is configured to engage the head component 12.

As described above, the instrument 100 also includes a pair of elongated arms 106 configured to engage the anchor 42 of the elongated stem component 14. Each arm 106 includes an elongated body 132 that extends from a distal end 134 to a proximal end 136. An engagement pin 138 extends outwardly from the distal end 134 of each arm 106 in a direction perpendicular or orthogonal to the axis 124 defined by the actuator 104. As shown in FIG. 3, the engagement pins 138 are shaped to be received in the passageway 62 defined in the elongated stem component 14.

The elongated arms 106 are coupled to the body 102 of the instrument 100 such that the arms 106 (and hence the engagement pins 138) may be repositioned relative to the axis 124. In the illustrative embodiment, the body 102 has a pair of channels 140 defined therein on each side of the elongated bore 108. Each channel 140 is sized to receive a corresponding proximal end 136 of one of the arm bodies 132. It should be appreciated that in other embodiments the instrument may include other combinations of tabs, openings, channels, or passageways to attach the arms to the body.

The instrument 100 also includes an adjustment mechanism 142 configured to permit the arms 106 to be selectively moved relative to the body 102 (and hence the axis 124). In the illustrative embodiment, the adjustment mechanism 142 includes a pair of screw clamps 144, 146 that may be operated by the user to independently position and fix each of the arms 106 at a desired position relative to the axis 124. It should be appreciated that in other embodiments the adjustment mechanism may include other fasteners, screws, tabs, and so forth configured to permit the arms to be selectively moved.

Figure 4:
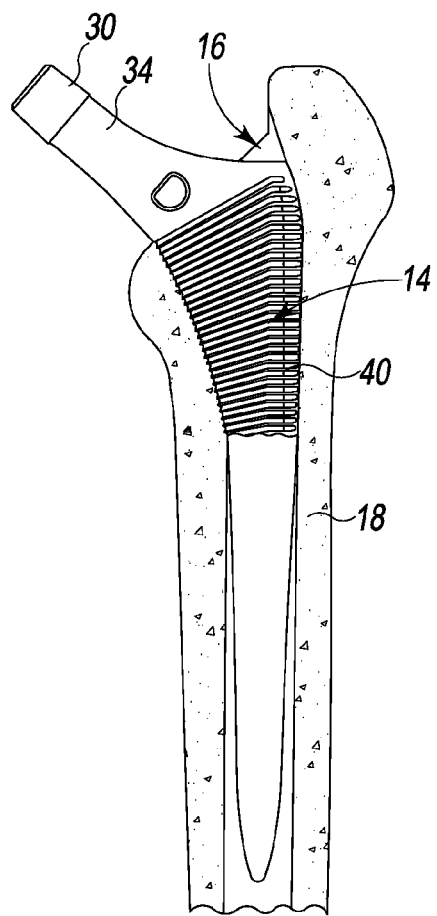
FIGS. 4-6 are views of a process of implanting the orthopaedic implant of FIG. 1 using the surgical instrument of FIG. 3.
Figure 5:
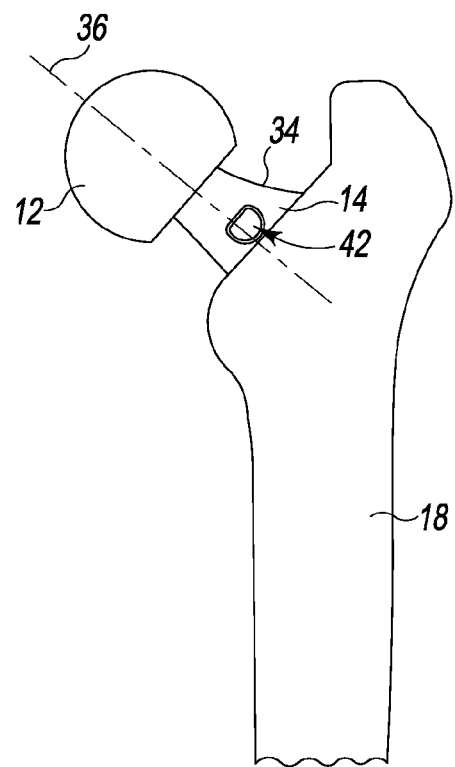

During a surgical procedure, the elongated stem component 14 may be inserted into a surgically-prepared intramedullary canal 16 of a patient's femur 18, as shown in FIG. 4. To attach a femoral head component 12, the surgeon may align the selected head component 12 with the trunnion 30 of the elongated stem component 14. The surgeon may advance the head component 12 along the longitudinal axis 36 such that the trunnion 30 is received in the tapered bore 28 defined in the head component 12.

A user, such as a surgeon or a surgical assistant, may then use the surgical instrument 100 to apply controllably a sufficient, quasistatic axial force to join the head component 12 to the stem component 14. A quasistatic axial force as used herein refers to an axial force that is applied gradually, increasing from a low to a high, peak magnitude. Conversely, a quasidynamic axial force as used herein refers to a high axial force that is applied, more or less, instantaneously, such as like a hammer strike.

To attach the surgical instrument 100, the user may operate the screw clamps 144, 146 to disengage the clamps 144, 146 from the proximal ends 136 of the elongated arms 106, thereby releasing the arms 106 for movement relative to the axis 124. The user may then pull the arms 106 away from the axis 124, which moves the engagement pins 138 apart. The engagement plate 116 may be advanced into the contact with the spherical outer surface 20 of the femoral head component 12, and the axis 124 aligned with the longitudinal axis 36 of the elongated neck 34 of the stem component 14.

Figure 6:
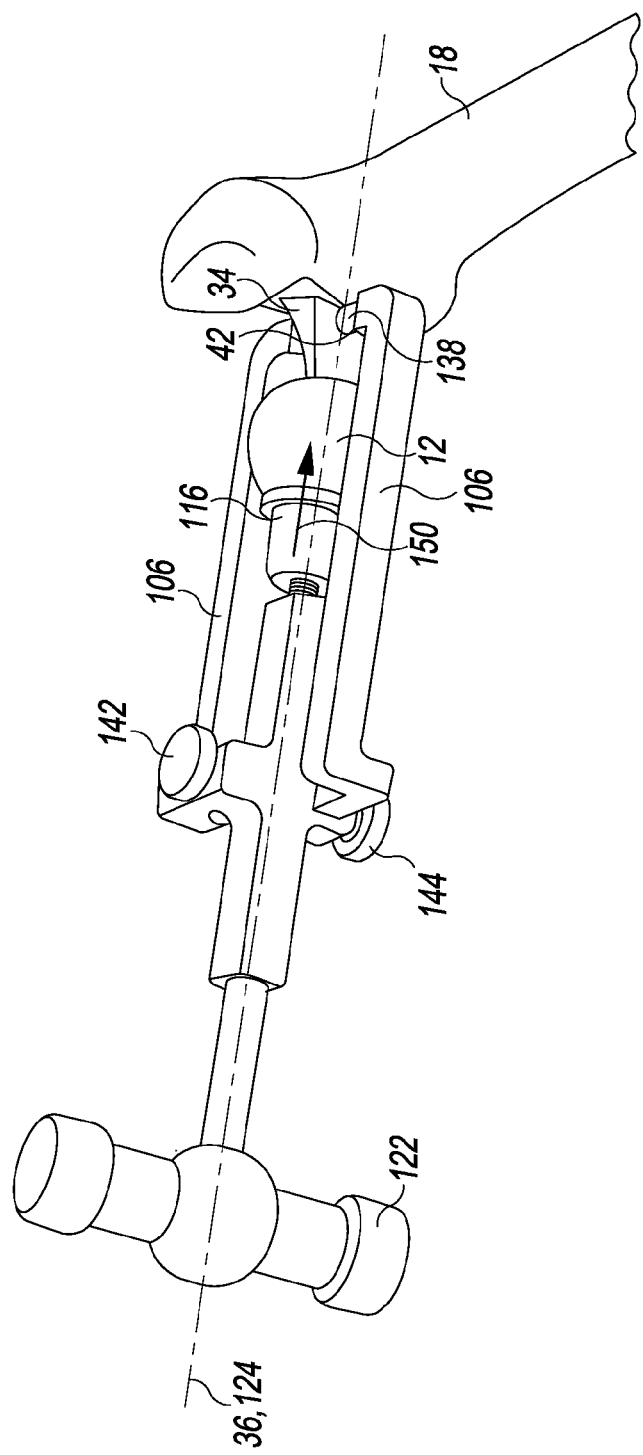

As shown in FIG. 6, the engagement pins 138 may be aligned with the passageway 62 defined in the stem component 14. The user may then advance the pins 138 into the passageway 62. When the pins 138 are positioned at the desired location, the user may operate the clamps 144, 146 to lock the elongated arms 106 (and hence the pins 138) into position. With the instrument 100 positioned as shown in FIG. 6, the user may rotate the handle 122 to advance the head component 12 along the aligned axes 36, 124 in the direction indicated by arrow 150. To exert the quasistatic axial force on the components 12, 14, the engagement pins 138 of the instrument 100 engage the medial surface 64 of the anchor 42 of the stem component 14 such that the actuator 104 applies a force to the components 12, 14 along the axes 36, 124 when the handle 122 is rotated.

In the illustrative embodiment, the instrument 100 is configured to apply at least a peak axial force of about 4 kN. It should be appreciated that in other embodiments the instrument may include a force gauge or other sensor to measure the force applied to the components 12, 14. After the user has applied a desired amount of force to secure the head component 12 to the stem component 14, the user may reverse actuator the instrument 100 and remove the instrument from the surgical area.

While the instrument 100 is illustrative hand-operated, it should be appreciated that in other embodiments the instrument 100 may include a motor or other drive mechanism to apply the axial force. Other surgical instruments configured to apply a quasistatic axial force are disclosed in U.S. Patent Application Ser. No. 62/103,611 entitled "ASSEMBLY TOOL," which is filed concurrently with this application. Such surgical instruments may be configured for use with specific, compatible types of anchors but may be adapted for use with the anchor 42 of the stem component 14. In other embodiments, the stem component may include other anchor configurations similar to those illustrated in FIGS. 7-13, which are described in greater detail below. Some features of the embodiments illustrated in FIGS. 7-13 are substantially similar to those discussed above in reference to the embodiment of FIGS. 1-6. Such features are designated in FIGS. 7-13 with the same reference numbers as those used in FIGS. 1-6.

Figure 7:
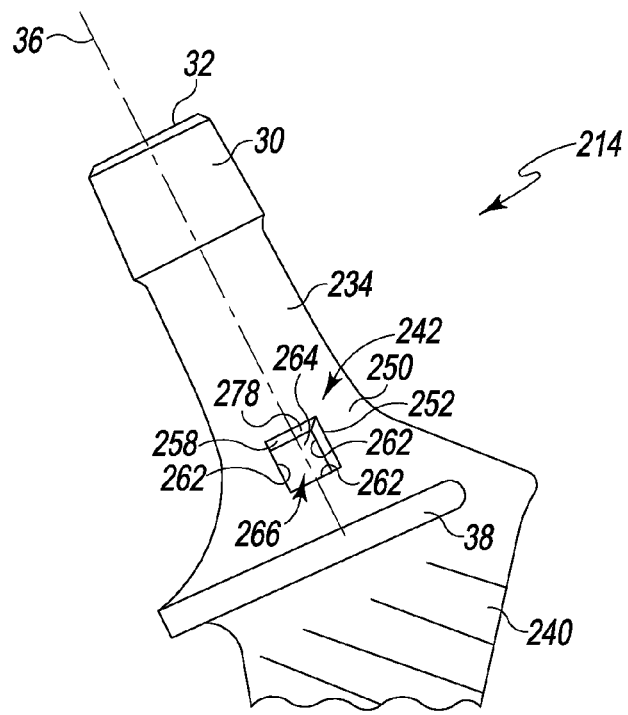
FIG. 7 is a side elevation view of another embodiment of an orthopaedic implant.
Figure 8:
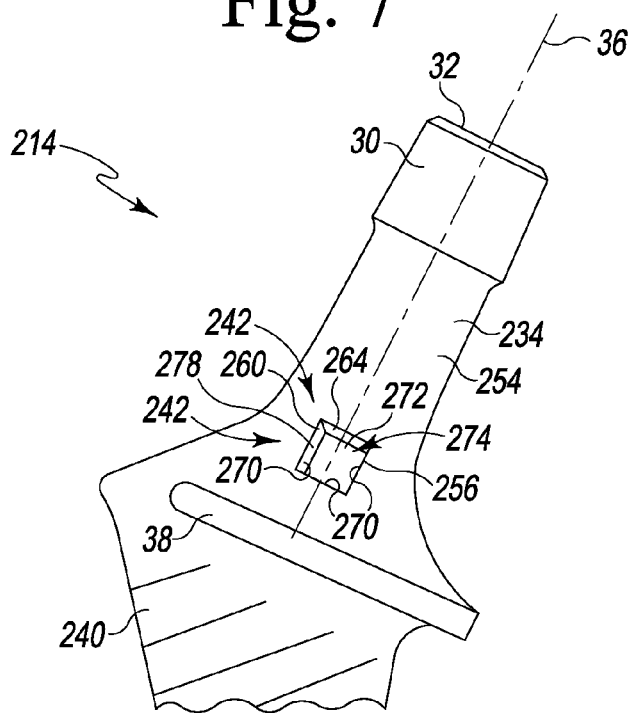
FIG. 8 is an opposite side elevation view of the embodiment of FIG. 7.

Referring now to FIGS. 7-8, another elongated stem component (hereinafter stem component 214) is shown. Similar to the embodiment of FIGS. 1-6, the stem component 214 includes a trunnion 30 formed in the end 32 of the elongated neck 234 of the stem component 214. The elongated neck 234 also has a longitudinal axis 36 that extends through the trunnion 30. As shown in FIG. 7, the elongated neck 234 extends medially and superiorly from an inferior end 38 attached to a proximal body 240 of the elongated stem component 214. Similar to the embodiment of FIGS. 1-6, a tapered stem (not shown) extends inferiorly away from the opposite end of the proximal body.

The elongated stem component 214 also includes a tool engagement feature or anchor 242 that is positioned on the neck 234. The anchor 242 of the elongated stem component 214 is defined in an anterior surface 250 and a posterior surface 254. The anterior surface 250 of the stem component 214 extends from the inferior end 38 of the neck 234 to the base of the trunnion 30, and an opening 252 is defined in the anterior surface 250 adjacent to the inferior end 38 of the neck 234. The posterior surface 254 extends from the inferior end 38 of the neck 234 to the base of the trunnion 30. Another opening 256 is defined in the posterior surface 250 adjacent to the inferior end 38 of the neck 34. In the illustrative embodiment, the anchor 242 includes an inner wall 258 that extends inwardly from the opening 252 and another inner wall 260 that extends inwardly from the opening 256.

As shown in FIGS. 7-8, the inner wall 258 is one of a plurality of inner walls 262 that extend from the opening 252 to a base surface 264. The base surface 264 and the inner walls 262 cooperate to define a closed aperture 266 in the anterior surface 250. Similarly, the inner wall 260 is one of a plurality of inner walls 270 that extend from the opening 256 to a base surface 272. The base surface 272 and the inner walls 270 cooperate to define a closed aperture 274 in the posterior surface 254. In the illustrated embodiment, the apertures 266, 274 are square-shaped. In other embodiments, the apertures may be rectangular, circular or other geometric shape.

In the illustrative embodiment, the inner walls 258, 260 include medial surfaces 278 that are substantially planar and are positioned in a common imaginary plane that extends through the elongated neck 234 orthogonal to the longitudinal axis 36. In other words, the medial surfaces 278, like the medial surface 64 of the stem component 14, extend orthogonal relative to the axis 36.

The anchor 242 of the stem component 214 may be engaged by an appropriately-shaped surgical instrument in a manner similar to that described above in regard to FIGS. 1-6. For example, the engagement pins 138 of the surgical instrument 100 may be shaped to be received in the closed apertures 266, 274 of the stem component 214 and thereby engage the anchor 242. In other embodiments, other surgical instruments may be used.

Figure 9:
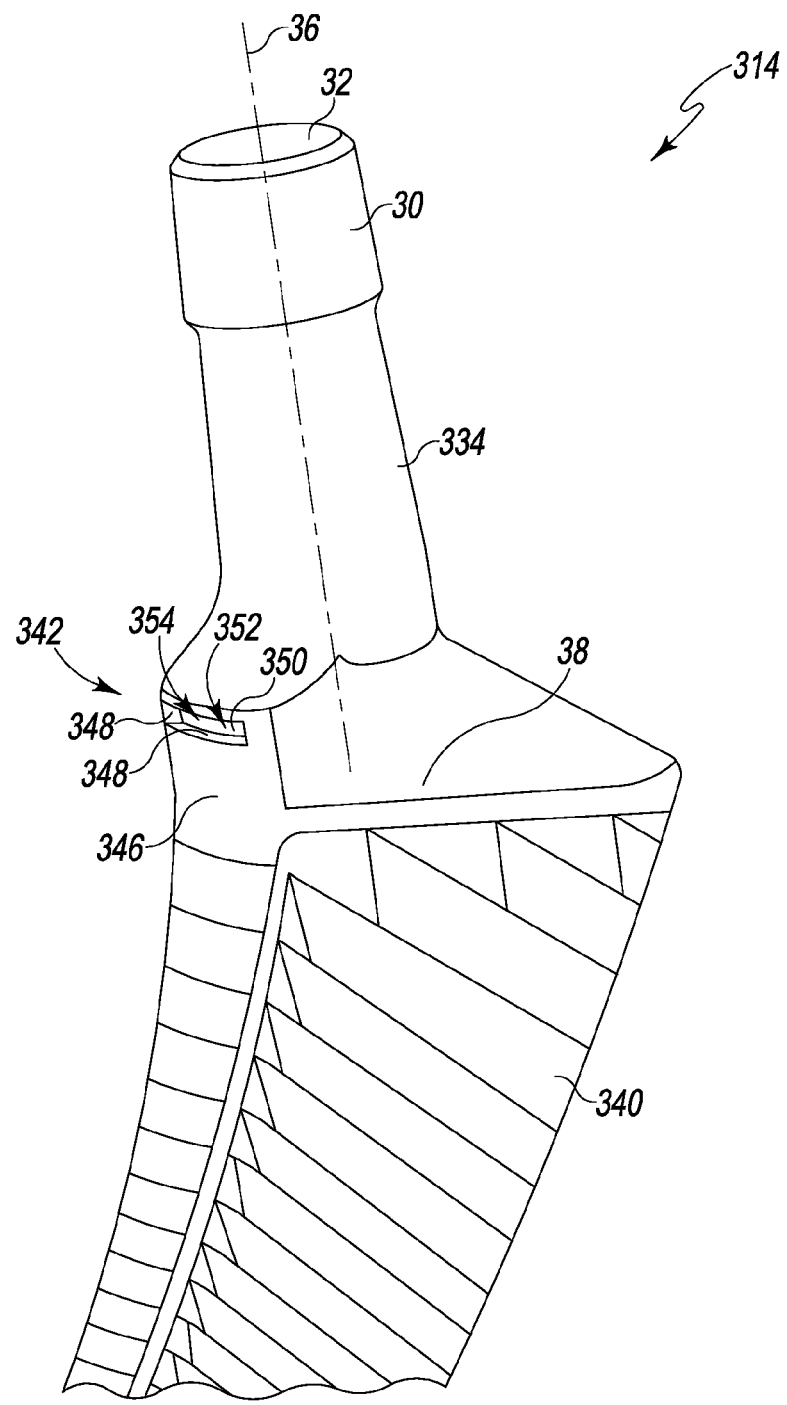
FIG. 9 is a perspective view of another embodiment of an orthopaedic implant.

Referring now to FIG. 9, another embodiment of an elongated stem component (hereinafter stem component 314) is shown. Similar to the embodiments of FIGS. 1-8, the stem component 314 includes a trunnion 30 formed in the end 32 of the elongated neck 334 of the stem component 314. The elongated neck 334 also has a longitudinal axis 36 that extends through the trunnion 30. As shown in FIG. 9, the elongated neck 334 extends medially and superiorly from an inferior end 38 attached to a proximal body 340 of the elongated stem component 314. A tapered stem (not shown) extends inferiorly away from the opposite end of the proximal body.

The elongated stem component 314 also includes a tool engagement feature or anchor 342 that is positioned on the neck 334. In the illustrative embodiment, the neck 334 has an opening 344 defined in a medial surface 346 at its inferior end 38. A number of inner walls 348 extend inwardly from the opening 344 to base surface 350. A closed pocket 352 is defined by the surfaces 350 and the inner walls 348. In the illustrated embodiment, the closed pocket 352 is rectangular-shaped. In other embodiments, the apertures may be square, circular or other geometric shape.

The anchor 342 includes a superior surface 354 of one of the inner walls 348. The superior surface 354 extends orthogonal to the longitudinal axis 36. In other embodiments, the surface 354 (and hence the anchor 342) may merely extend transverse to the axis 36. The superior surface 354 may be engaged by an appropriately-shaped surgical instrument in a manner similar to that described above in regard to FIGS. 1-8. For example, the surgical instrument 100 may be configured with only a single engagement pin 138 that is shaped to be received in the closed pocket 352 of the stem component 314 and thereby engage the superior surface 354 of the anchor 342. In other embodiments, other surgical instruments may be used.

Figure 10:
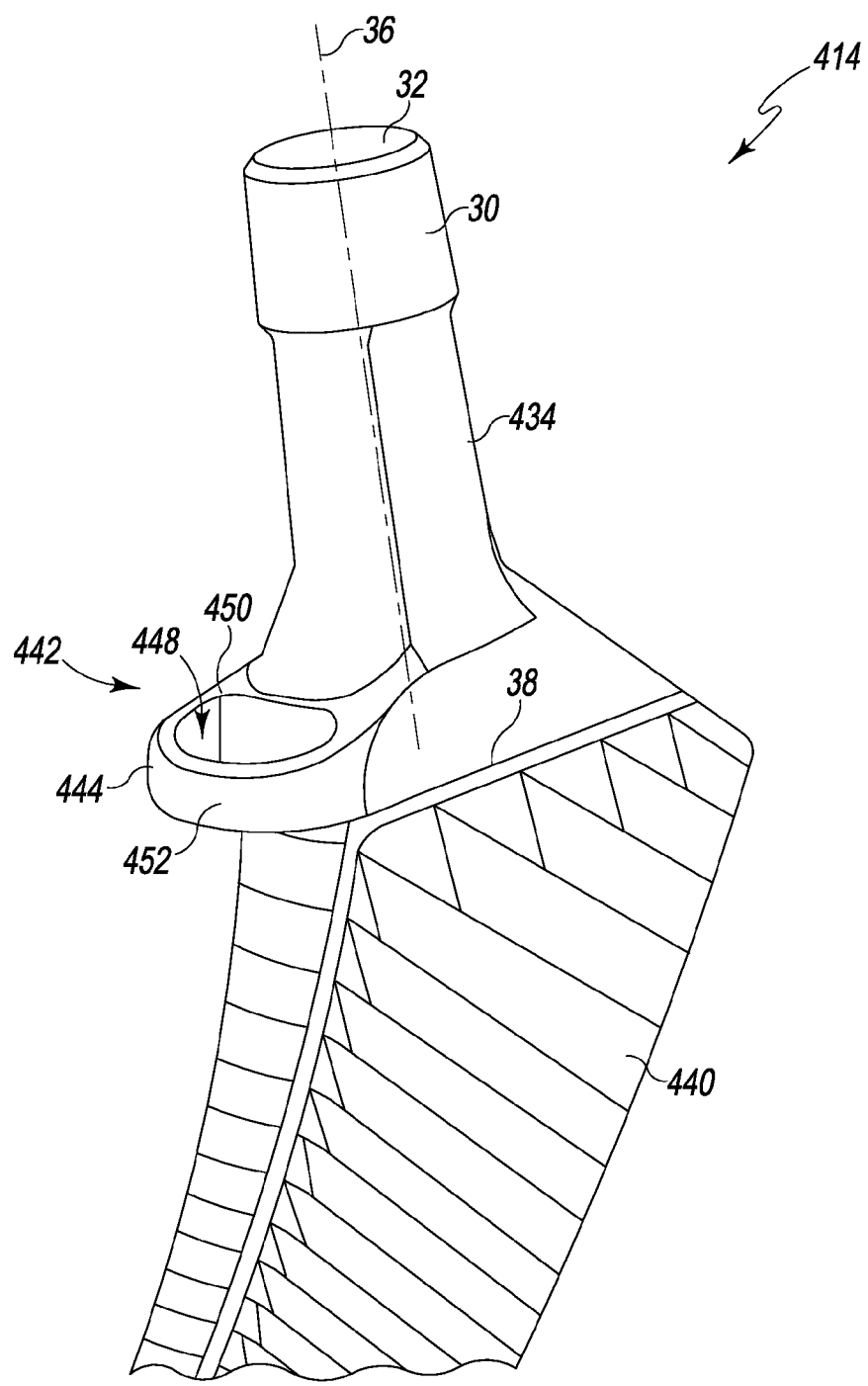
FIG. 10 is a perspective view of another embodiment of an orthopaedic implant.

Referring now to FIG. 10, another embodiment of an elongated stem component (hereinafter stem component 414) is shown. Similar to the embodiments of FIGS. 1-8, the stem component 414 includes a trunnion 30 formed in the end 32 of the elongated neck 434 of the stem component 414. The elongated neck 434 also has a longitudinal axis 36 that extends through the trunnion 30. As shown in FIG. 10, the elongated neck 434 extends medially and superiorly from an inferior end 38 attached to a proximal body 440 of the elongated stem component 414. A tapered stem (not shown) extends inferiorly away from the opposite end of the proximal body.

The elongated stem component 414 also includes a tool engagement feature or anchor 442 that is positioned on the neck 434. In the illustrative embodiment, the neck 434 has a collar 444 that extends outwardly from a medial surface 446 at its inferior end 38. As shown in FIG. 10, the collar 444 has a slot 448 extending from a superior opening 450 to an inferior opening (not shown) and a curved outer surface 452. The slot 448 is sized to receive an appropriately sized surgical instrument. In other embodiments, the slot may be omitted.

The collar 444 extends orthogonal to the longitudinal axis 36, and may be engaged by an appropriately-shaped surgical instrument in a manner similar to that described above in regard to FIGS. 1-9. For example, the surgical instrument 100 may be configured with only a single engagement pin 138 that is shaped to engage the collar 444 of the anchor 442. In other embodiments, other surgical instruments may be used.

Figure 11:
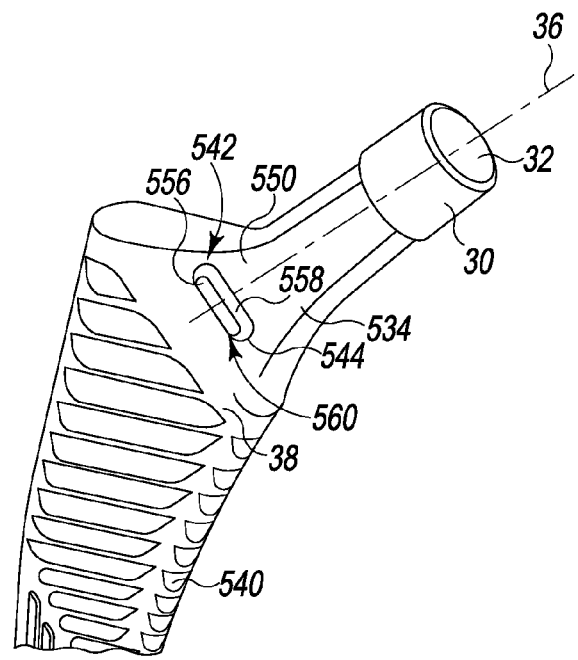
FIG. 11 is a first side perspective view of another embodiment of an orthopaedic implant.
Figure 12:
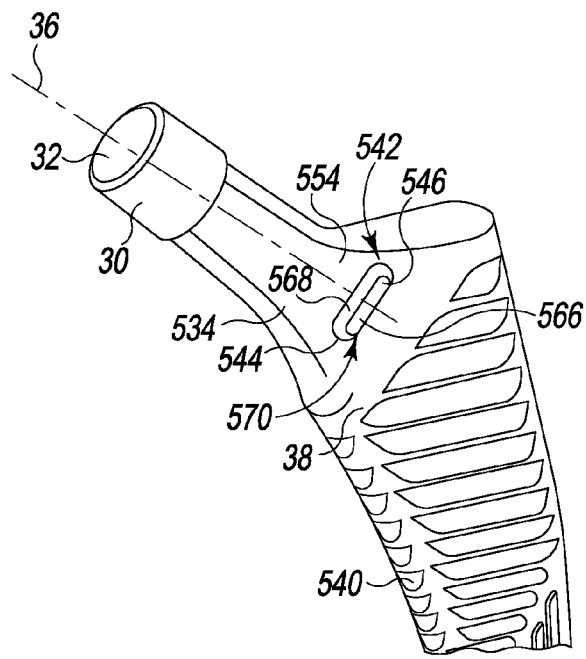
FIG. 12 is a second side perspective view of the embodiment of FIG. 11.

Referring now to FIGS. 11-12, another elongated stem component (hereinafter stem component 514) is shown. Similar to the embodiments of FIGS. 1-10, the stem component 514 includes a trunnion 30 formed in the end 32 of the elongated neck 534 of the stem component 214. The elongated neck 534 also has a longitudinal axis 36 that extends through the trunnion 30. As shown in FIG. 11, the elongated neck 534 extends medially and superiorly from an inferior end 38 attached to a proximal body 540 of the elongated stem component 514. A tapered stem (not shown) extends inferiorly away from the opposite end of the proximal body.

The elongated stem component 514 also includes a tool engagement feature or anchor 542 that is positioned on the neck 534. The anchor 542 of the elongated stem component 514 includes a pair of flanges 544, 546 that extend outwardly from an anterior surface 550 and a posterior surface 554, respectively. As shown in FIG. 11, the anterior surface 550 of the stem component 514 extends from the inferior end 38 of the neck 534 to the base of the trunnion 30, and the flange 544 extends outwardly from the surface 550 adjacent to the inferior end 38 of the neck 534. The flange 544 includes an elongated body 556 that extends orthogonal to the axis 36. The flange 544 also includes a superior surface 558 and an inferior surface 560.

As shown in FIG. 12, the posterior surface 554 extends from the inferior end 38 of the neck 534 to the base of the trunnion 30. The flange 546 extends outwardly from the surface 554 adjacent to the inferior end 38 of the neck 534. The flange 546 includes an elongated body 566 that extends orthogonal to the axis 36. The flange 546 also includes a superior surface 568 and an inferior surface 570.

In the illustrative embodiment, the inferior surfaces 560, 570 are substantially planar and are positioned in a common imaginary plane that extends through the elongated neck 534 orthogonal to the longitudinal axis 36. In other words, the inferior surfaces 560, 570, like the medial surface 64 of the stem component 14, extend orthogonal relative to the axis 36.

The anchor 542 (i.e., the flanges 544, 546) of the stem component 514 may be engaged by an appropriately-shaped surgical instrument in a manner similar to that described above in regard to FIGS. 1-10. For example, the engagement pins 138 of the surgical instrument 100 may be shaped to engage the flanges 544, 546. In other embodiments, other surgical instruments may be used.

Figure 13:
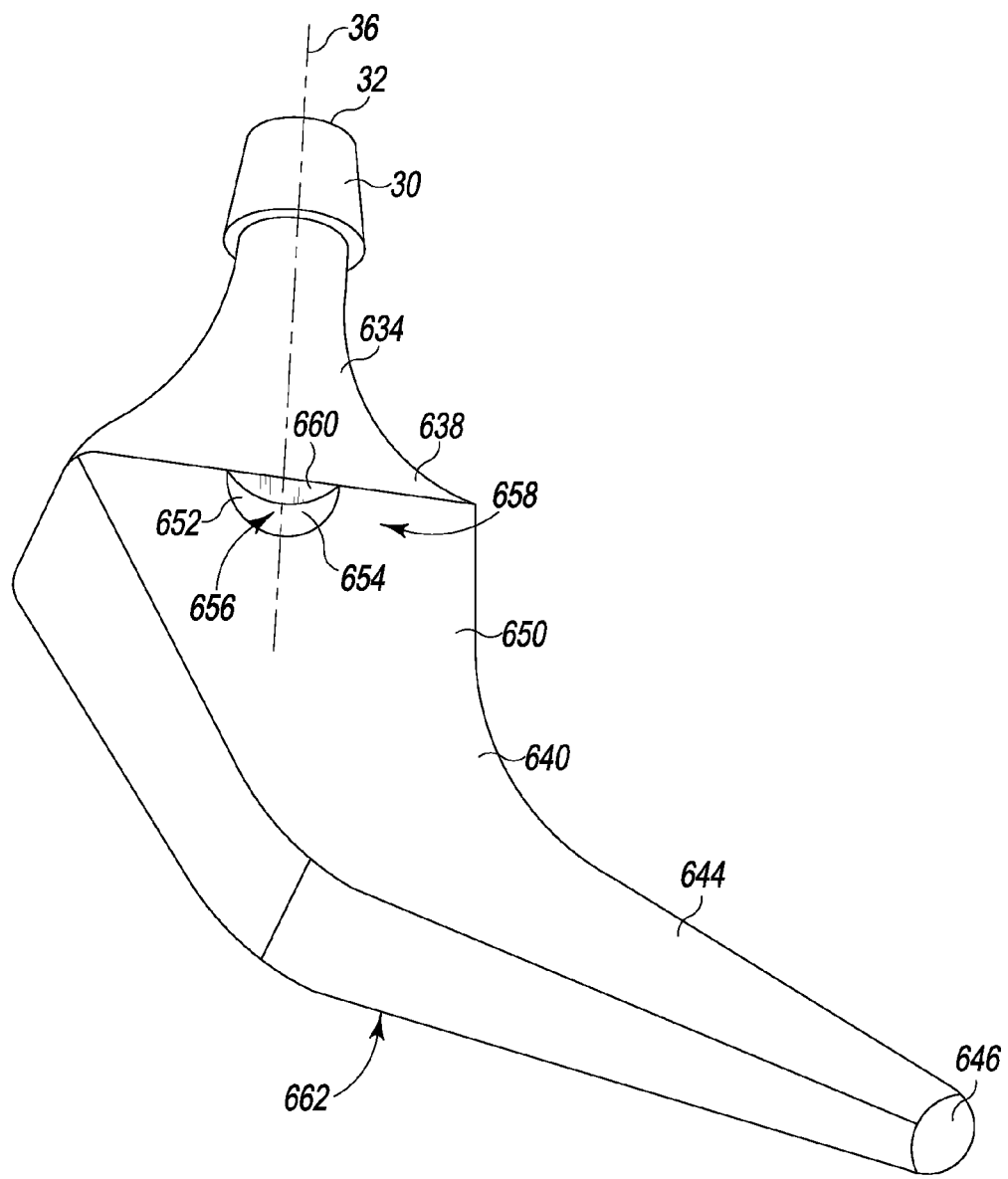
FIG. 13 is a perspective view of another embodiment of an orthopaedic implant.

Referring now to FIG. 13, another elongated stem component (hereinafter stem component 614) is shown. Similar to the embodiments of FIGS. 1-12, the stem component 614 includes a trunnion 30 formed in the end 32 of the elongated neck 634 of the stem component 614. The elongated neck 634 also has a longitudinal axis 36 that extends through the trunnion 30. As shown in FIG. 11, the elongated neck 234 extends medially and superiorly from an inferior end 638 attached to a proximal body 640 of the elongated stem component 214. A tapered stem 644 extends inferiorly away from the opposite end of the proximal body 640 to a distal end 646.

The elongated stem component 614 also includes a tool engagement feature or anchor 642. In the illustrative embodiment, the anterior surface 650 of the proximal body 640 has an opening 652 defined therein. An inner wall 654 extends inwardly from the opening 652 to define a closed aperture 656 in the body 640. As shown in FIG. 13, the aperture 656 has an open end 658 that is closed by an inferior surface 660 of the elongated neck 634.

The anchor 642 includes the inferior surface 660. The anchor 642 also includes another inferior surface (not shown) defined on the posterior side 662 of the stem component 614. In the illustrative embodiment, the inferior surfaces 660 are substantially planar and are positioned in a common imaginary plane that extends through the elongated neck 634 orthogonal to the longitudinal axis 36.

The anchor 642 of the stem component 614 may be engaged by an appropriately-shaped surgical instrument in a manner similar to that described above in regard to FIGS. 1-6. For example, the engagement pins 138 of the surgical instrument 100 may be shaped to be received in the closed apertures 656 of the stem component 614 and thereby engage the anchor 642. In other embodiments, other surgical instruments may be used.

It should be appreciated that the anchors of the stem components described above may be configured for use in other parts of the orthopaedic surgical procedure. For example, a surgeon may use the anchors to grip the stem during implantation and extraction, thereby eliminating the need for a separate feature to perform that step.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. A system for hip orthopaedic surgery, the system comprising:
   a femoral head component, an elongated stem component comprising: (i) a proximal body, (ii) a neck extending superiorly and medially from the proximal body, the neck having a longitudinal axis and being configured to receive the femoral head component, (iii) a tapered stem extending inferiorly from the proximal body, (iv) a first opening defined in an anterior surface of the neck, (v) a second opening defined in a posterior surface of the neck, and (vi) an anchor positioned on the neck and extending orthogonal to the longitudinal axis of the neck, the anchor having a first inner wall extending inwardly from the first opening and a second inner wall extending inwardly from the second opening, and each of the first and second inner walls includes a planar medial surface that extends orthogonal to the longitudinal axis of the neck and a curved surface connected to the planar medial surface, and a surgical instrument including (i) a plate configured to engage the femoral head component, (ii) an arm configured to engage the anchor to secure the surgical instrument to the elongated stem component, the arm including a planar surface shaped to engage at least one of the planar medial surfaces of the elongated stem component, and (iii) an actuator configured to move the plate along an axis to apply a force to the femoral head component to advance the femoral head component onto the neck.

2. The system of claim 1, wherein the first inner wall and the second inner wall cooperate to define a passageway extending between the first opening and the second opening.

3. The system of claim 1, wherein:
the femoral head component includes a tapered bore, and
the neck includes a tapered trunnion sized to receive the tapered bore.

4. A system for hip orthopaedic surgery, the system comprising:
a femoral head component,
an elongated stem component comprising: (i) a proximal body, (ii) a neck extending superiorly and medially from the proximal body, the neck having a longitudinal axis and being configured to receive the femoral head component, (iii) a tapered stem extending inferiorly from the proximal body, (iv) a first opening defined in an anterior surface of the neck, (v) a second opening defined in a posterior surface of the neck, and (vi) an anchor positioned on the neck and extending orthogonal to the longitudinal axis of the neck, the anchor having an inner wall that extends between the first opening and the second opening to define a passageway, the inner wall including a planar medial surface and a curved surface connected to the planar medial surface, and a surgical instrument including (i) a plate configured to engage the femoral head component, (ii) an arm configured to engage the anchor to secure the surgical instrument to the elongated stem component, the arm including a planar surface shaped to engage the planar medial surface of the elongated stem component, and (iii) an actuator configured to move the plate along an axis to apply a force to the femoral head component to advance the femoral head component onto the neck, wherein the planar medial surface includes a pair of edges and a midpoint positioned between the pair of edges, and the longitudinal axis of the neck intersects the planar medial surface at the midpoint.

5. The system of claim 4, wherein:
the femoral head component includes a tapered bore, and
the neck includes a tapered trunnion sized to receive the tapered bore.

6. The system of claim 4, wherein the planar medial surface extends orthogonal to the longitudinal axis of the neck.

* * * * *